United States Patent
Perry

(10) Patent No.: US 9,468,597 B1
(45) Date of Patent: Oct. 18, 2016

(54) STABILIZED L-ASCORBIC ACID SKIN SERUM

(71) Applicant: Arthur William Perry, Belle Mead, NJ (US)

(72) Inventor: Arthur William Perry, Belle Mead, NJ (US)

(73) Assignee: Dr. Perry Skindustries, LLC, Belle Meade, NJ (US)

( * ) Notice: Subject to any disclaimer, the term of this patent is extended or adjusted under 35 U.S.C. 154(b) by 221 days.

(21) Appl. No.: 14/217,331

(22) Filed: Mar. 17, 2014

Related U.S. Application Data

(60) Provisional application No. 61/802,446, filed on Mar. 16, 2013.

(51) Int. Cl.
| | |
|---|---|
| *A61K 36/53* | (2006.01) |
| *A61K 36/185* | (2006.01) |
| *A61K 36/28* | (2006.01) |
| *A61K 8/97* | (2006.01) |
| *A61K 8/67* | (2006.01) |
| *A61K 8/365* | (2006.01) |
| *A61Q 19/00* | (2006.01) |
| *A61K 8/19* | (2006.01) |
| *A61K 8/362* | (2006.01) |
| *A61K 8/49* | (2006.01) |

(52) U.S. Cl.
CPC . *A61K 8/97* (2013.01); *A61K 8/19* (2013.01); *A61K 8/362* (2013.01); *A61K 8/365* (2013.01); *A61K 8/498* (2013.01); *A61K 8/671* (2013.01); *A61K 8/676* (2013.01); *A61Q 19/00* (2013.01)

(58) Field of Classification Search
None
See application file for complete search history.

(56) References Cited

U.S. PATENT DOCUMENTS

| | | | | |
|---|---|---|---|---|
| 5,648,395 A | * | 7/1997 | Yu | A61K 8/26 514/574 |
| 2014/0315995 A1 | * | 10/2014 | Dreher | A61K 31/375 514/458 |

FOREIGN PATENT DOCUMENTS

| | | | | |
|---|---|---|---|---|
| KR | 2009027295 A | * | 3/2009 | |
| WO | WO 2010030636 A1 | * | 3/2010 | A61K 8/06 |

* cited by examiner

*Primary Examiner* — Chris R Tate
*Assistant Examiner* — Randall Winston
(74) *Attorney, Agent, or Firm* — Fanelli Haag PLLC

(57) ABSTRACT

An aqueous topical serum having stabilized bioactive L-ascorbic acid has a pH of from 3.4 to 3.8 and comprises from 10% to 18% by weight of L(+)-ascorbic acid, 0.2% by weight retinyl propionate, and from 0.005% to 0.5% by weight of a mixture selected from the group consisting of glabridin, silibinin and thyme.

23 Claims, No Drawings

STABILIZED L-ASCORBIC ACID SKIN SERUM

CROSS REFERENCE TO RELATED APPLICATIONS

This application is related to, and claims priority of, U.S. Application Ser. No. 61/802,446, filed Mar. 16, 2013, the entire contents of which are incorporated herein by reference.

FIELD OF THE INVENTION

The present invention relates to skin rejuvenating topical compositions. More particularly, the present invention relates to formulations of L-ascorbic acid in which the l-ascorbic acid is pH stabilized in aqueous form, together with other important skin rejuvenating and skin protecting ingredients, to retain substantial efficacy after long periods of time.

BACKGROUND

It is fairly well established that, over time, human skin is ravaged by the effects of age, poor nutrition, exposure to sunlight and other harsh external factors. It is also fairly well established that applying topical compositions including nutrients (such as vitamins A, B, C, D, E and K and their related molecules and derivatives), UV protectants, moisturizers and anti-oxidants for protection and repair of the skin is often the best way to administer relatively copious amounts of select healing and protectant substances without adversely affecting internal tissues. However, providing topical compositions comprising [a] beneficial mixtures comprising [b] effective quantities of these ingredients, in a form which will [c] be skin permeable and bioavailable, yet [d] found pleasing to a consumer from a variety of aesthetic considerations including smell, feel, color, ease of application; [e] retain its beneficial quantities for an adequate amount of time, i.e. shelf-life; and [f] be commercially viable, i.e. cost-effective, is a task which is part artistry, part chemistry and has been for literally thousands of years.

In particular, certain of the most desirable skin nutrients, such as l-ascorbic acid, are very easily oxidized and thus highly sensitive to pH and UV radiation, among other factors, thereby severely limiting the excipients and co-ingredients with which they may be delivered and still remain beneficial. Additionally, l-ascorbic acid is most biologically active in aqueous form, Traikovich, S. S., Use of topical ascorbic acid and its effect on photodamaged skin topography. Arch. Otolaryngol. Head Neck Surg. 125, 1091-1098, 1999. which is unfortunately also the form in which it is most susceptible to oxidation and shortened shelf life, rapidly degrading and turning brown, rendering topical products aesthetically displeasing and commercially useless. These disadvantages, i.e. rapid product discoloration, short shelf life, rapid oxidation, have made it difficult to provide a topically administered aqueous skin composition incorporating l-ascorbic acid.

Non-aqueous delivery vehicles incorporating l-ascorbic acid suffer from other disadvantages including miscibility, product release and absorption, and messy residue. Trying to stabilize vitamin C by use of microencapsulation in an aloe gel base adds considerable complexity and expense to skin rejuvenation products. Furthermore, deposition of the l-ascorbic acid payload into the skin may be very difficult to achieve in doses which are optimal for a therapeutic response, i.e. 30-40% higher than normal tissue levels.

Retinoids, which are derivatives of vitamin A, are another subset of nutrients which are highly beneficial to the health and appearance of skin, but which are also highly subject to oxidation and inactivation by sunlight, particularly retinoic acid.

SUMMARY OF THE INVENTION

Because of ascorbic acid's and retinoids' sensitivity to UV light, the serum of the exemplary embodiments are meant to be applied at night so absorption and integration into the skin can take place before the active ingredients are rendered ineffective.

DEFINITIONS

The following terms are used herein according to the following definitions.

"Effective amount" means the amount of the one or more components when in a composition, as a whole, provides "Hydrophilic" or "water-soluble" refers to a material that will disperse or dissolve in deionized water (or other aqueous solution as specified) at a temperature of 23.degree. C. in an amount of at least 7% by weight, preferably at least 10% by weight, more preferably at least 20% by weight, even more preferably at least 25% by weight, even more preferably at least 30% by weight, and most preferably at least 40% by weight, based on the total weight of the hydrophilic material and the water. The component is considered dissolved if after thoroughly mixing the compound with water at 60.degree. C. for at least 4 hours and allowing this to cool to 23-25.degrees. C. for 24 hours, and mixing the composition thoroughly it appears uniform clear solution without visible cloudiness, phase separation, or precipitate in a jar having a path length of 4 cm. Typically, when placed in a 1×1 cm cell, the samples exhibit greater than 70% transmission measured in a suitable spectrophotometer at a wavelength of 655 nm. Water dispersible hydrophilic materials disperse in water to form uniform cloudy dispersions after vigorous shaking of a 5% by weight mixture of the hydrophilic component in water. Preferred hydrophilic components are water-soluble.

"Hydrophobic" or "water-insoluble" refers to a material that will not significantly dissolve in deionized water at 23.degree. C. "Not significantly" means that the solubility in water of the material is less than 5% by weight, preferably less than 1% by weight, more preferably less than 0.5% by weight, and even more preferably less than 0.1% by weight, based on the total weight of the hydrophobic material and the water. Solubility can be determined by thoroughly mixing the compound with water at the appropriate concentration at 23.degree. C. for at least 24 hours (or at elevated temperature if that is necessary to dissolve the compound), allowing this to sit at 23-25.degree. C. for 24 hours, and observing the sample. In a glass jar with a 4 cm. path length the sample should have evidence of a second phase which can be liquid or solid and may be separated on the top, bottom, or distributed throughout the sample. For crystalline compounds care must be taken to avoid producing a supersaturated solution. The components should be mixed and observed. Cloudiness or presence of a visible precipitate or separate phase indicates that the solubility limit has been exceeded. Typically when placed in a 1×1 cm. cell the sample has less than 70% transmission measured in a suitable spectrophotometer at a wavelength of 655 nm. For solubility determinations less than that which can be observed with the naked eye, the solubility is determined using radiolabeled compounds as described under "Conventional Solubility Estimations" in Solubility of Long-Chain Fatty Acids in Phosphate Buffer at pH 7.4, Henrik Vorum, et. al., Biochimica et. Biophysica Acta. 1126 (1992) 135-142.

"Stable" means physically stable or chemically stable, which are both defined in greater detail below. Preferred compositions are both chemically and physically stable.

The terms "comprises" and variations thereof do not have a limiting meaning where these terms appear in the description and claims.

As used herein, "a," "an," "the," "at least one," and "one or more" are used interchangeably. The term "and/or" means one or all of the listed elements (e.g., preventing and/or treating an affliction means preventing, treating, or both treating and preventing further afflictions).

Also herein, the recitations of numerical ranges by endpoints include all numbers subsumed within that range (e.g., 1 to 5 includes 1, 1.5, 2, 2.75, 3, 3.80, 4, 5, etc.).

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DETAILED DESCRIPTION OF THE INVENTION

Exemplary embodiments of the disclosed invention are serums comprising mixtures of biologically active substances that are proven to improve the appearance of the skin. The mixtures are selected from specific forms of vitamins C and A, alpha-hydroxy acids (AHAs), antioxidants and tyrosinase inhibitors.

In a preferred embodiment, the antioxidant and tyrosinase inhibitor are *Glycyrrhiza Glabra* (Licorice) root extract and silybinin, an extract from milk thistle.

The unique combinations of these active agents comprise powerful skin rejuvenators having optimal activity levels and lasting shelf life due to ingredients and processes which guarantee optimal pH levels, and feature ease of use and comfort for enhanced user compliance.

Exemplary embodiments of the disclosed invention are sera, as opposed to a creams, gels, or ointments. A serum base is preferably designed to deliver the active ingredients and leave minimal residue. Ideally, the base is designed to dry within about 20 seconds of application, thereby minimizing the chance of liquid vitamin C remaining, which could stain a user's clothes or bedlinens.

Exemplary formulations of the present invention maintain a pH within a range of from 3.2 to about 3.8 and preferably at a pH of about 3.5, the level required for L-ascorbic acid to physiologically function at its peak activity.

Exemplary formulations and processes used for making them are selected with the goal of combining ingredients having physical and chemical properties and using physical and chemical methods which preserve the L-ascorbic acid. Exemplary embodiments of the inventive formulations have achieved acceptable product shelf life, as measured by achieving a minimum of percentage of at least 8% by weight active vitamin C remaining after accelerated storage testing, of at least 6 months, preferably at least 9 months, and most preferably at least 12 months.

Vitamin C is one of the main anti-oxidants in the body. As an anti-oxidant, vitamin C fights injury to our cells by neutralizing "free radicals". Without exposure to light, vitamin C has a half-life of about 4 day. However, not all vitamin C is created equal. It is well established that the preferred form of vitamin C for utilization by the body is L-ascorbic acid.

Vitamin C can protect against ultraviolet A and B light sunburn, reduce sun—induced wrinkling, and decrease skin cancers. As a powerful antioxidant, it decreases dangerous oxygen free radicals and inflammation and decreases sunburn after sun exposure. It is more effective when used along with a sunblock. It can decrease the redness associated with acne rosacea after just three weeks of use. Vitamin C decreases brown pigmentation in the skin by slowing its formation. It is extremely effective in reducing melasma, a resistant type of hyperpigmentation. Vitamin C promotes collagen synthesis, leading to a thicker, healthier dermis in the skin. Vitamin C significantly improves sun-induced aging and decreases wrinkles and increases elastin in the skin. These changes are visible clinically and under the microscope.

The skin also needs vitamin A. Without it, skin becomes dry and the hair and nails become brittle. Vitamin A and retinoic acid act on DNA—they actually change the genes that control skin cells. Retinoic acid decreases acne and visible pore size, increases elastin and hyaluronic acid, hydrates the skin, makes the skin firmer and more elastic, lessens dark circles around the eyes.

Retinoic acid is also a first line treatment for acne and rosacea and seborrheic dermatitis. Retinoids not only can repair sun damaged skin, but may prevent it. Their use has been shown to result in smoother, less wrinkled, skin, to lessen actinic keratoses (premalignant lesions) and prevent skin cancer. Retinoid acid is reported to stimulate the formation of collagen, decrease the brown pigmentation in the skin, and, in one study, to improve stretch marks. While the human body can utilize only a very specific form of vitamin C (L-ascorbic acid), humans have enzymes that are capable of converting various forms of vitamin A, including retinyl propionate, into retinoic acid, the active form.

To have optimal biologic function, L-ascorbic acid must be maintained in an environment having most preferably a pH of 3.5. Additionally, there is a "dose-response curve" for L-ascorbic acid, and the optimal concentration required to see an effect is 10%, by weight. Thus, for topical use, vitamin C must be delivered and maintained in contact with the skin at a concentration of at least 8% by weight. No pathological effects have been observed when it is placed on the skin. Neither an 18% nor a 10% concentration irritated the skin when placed under a patch for 4 days. Thus providing a serum in a concentration of from 10% to about 18% will provide the desired results without causing skin irritation, and preferably at a pH of 3.5, and in the L-stereoisomer form.

Vitamin C, much like Vitamin A, is rapidly destroyed by light. For this reason, it must be constantly replaced in the skin for maximal effect. High levels of vitamin C can be attained safely and most effectively only with topical application. Applying the exemplary embodiments of compositions of the present invention, intradermal concentrations of vitamin C that are 20-40 times higher than normal skin tissue levels that are safely achievable by systemic administration normal. Higher concentrations provide the skin with a reservoir of this important antioxidant that, once absorbed, will impart its benefits for periods lasting days or until inactivated by ultraviolet radiation. Safe daily administration ensures the maintenance of the needed high intradermal levels with no toxicity or untoward effects observed.

The combination of both vitamin A and vitamin C reverses skin changes caused by aging and sun damage more than either alone. Compositions of the exemplary embodiments contain select forms of both vitamin A and vitamin C. There are a number of vitamin A-type substances that are used in skin creams, called retinoids. The most common is retinoic acid—the ingredient in Retin-A®. The exemplary embodiments of the present invention use an ester of retinoic acid called retinyl propionate. The ester form is converted to retinoic acid by enzymes in the skin.

The over-the-counter retinol type drugs have effects similar to retinoid acid. Other vitamin A drugs like retinyl propionate, retinyl palmitate and retinaldehyde also work even at low concentrations. Retinyl propionate is less irritating than the retinol that is commonly found in over-the-counter skin creams. It has been shown that retinyl esters do not have to be irritating in order to be effective. In fact, retinyl propionate is converted within the skin, first to retinol, then to retinaldehyde, and then to the active form—retinoic acid. All this is done by the enzymes that are already in your skin. Thus retinyl propionate may be administered and impart the same benefits as retinoic acid due to its conversion to retinoic acid within the skin.

Retinyl propionate has been conclusively shown to decrease premalignant lesions, called actinic keratoses, if used for 48 weeks. Retinyl propionate is a storage form of vitamin A that concentrates in the epidermis. Retinoids are lipophilic—that is they are fat soluble and easily penetrate the epidermis. Retinyl propionate renews epidermal cells, filters ultraviolet light, prevents oxidative stress by acting as an antioxidant, controls bacteria in the skin, and improves skin aging.

Retinyl esters absorb ultraviolet radiation and protect from these rays. Additionally, skin creams that contain vitamin A are not absorbed into the blood, hence safe for all people when administered topically. Unfortunately, retinoids degrade when exposed to the ultraviolet light of the sun. They also degrade rapidly when stored at temperatures over 100 degrees.

The serums of the exemplary embodiments contain from 6% to as much as 10%, but preferably 8% L(+)-Lactic Acid aqueous solution having a pH of 2. This fruit acid is derived from milk and is one of the alpha-hydroxy acids (AHAs). It has been studied since 1974. Other naturally occurring AHAs are glycolic acid from sugar cane, citric acid from fruit, and malic acid from apples. There are also other AHAs that are made synthetically in laboratories.

AHAs cause shedding of the upper layers of the skin, a process called exfoliation or desquamation, possibly by chelating calcium and weakening the connections between cells. This smooths the skin and decreases acne by keeping the pores clean. It improves dry skin, rough skin acne, rosacea, and improves wrinkles and sun damaged skin. Superficial brown pigmentation is decreased by exfoliation.

The chemical spurs collagen production, calms inflammation and is an antioxidant. Its effects remain for 2-3 weeks after stopping. Sunblock must be applied to the skin during the day for a week after AHA use.

While lactic acid is considered an exfoliant, facilitating the shedding of dead stratum corneal cells, it also has an antiproliferative effect on skin cells. This contributes to a smooth feeling skin.

Lactic acid in the 5% concentration can improve the skin barrier by exfoliating and increasing the number and secretin of lamellar bodies, which are known to be the critical structure for barrier function in the epidermis.

Lactic acid, in this preparation, is used not only to smooth rough skin (exfoliation), but to enhance the penetration of the other active agents in the serum. Lactic acid is a percutaneous penetration enhancer for hydrophilic molecules such as L-ascorbic acid and retinyl propionate, but it does not irritate the skin while performing this function.

AHAs are well known to increase the bioavailability of retinoids, and so the inclusion of lactic acid in this formula increases the bioavailability of the retinyl propionate. This has been shown in studies to control acne vulgaris. AHAs are also known to increase the collagen and hyaluronic acid content of skin and AHAs, specifically lactic acid, decrease melanin in the upper and lower levels of the skin.

Lactic acid increases skin cell renewal and moisture content of the skin and reduces wrinkles over a 6 week period. Treatment with AHAs caused an approximate 25% increase in skin thickness. The epidermis was thicker and papillary dermal changes included increased thickness, increased acid mucopolysaccharides, improved quality of elastic fibers, and increased density of collagen. No inflammation was evident.

Citric acid 2% is a natural antibacterial. Citric acid also increases the thickness of the epidermis and dermal glycocosaminoglycans.

What has not been heretofore appreciated is that citric acid and lactic acid can help to stabilize L-ascorbic acid.

Glabridin, a light sensitive chemical and one of the main components of *Glycyrrhiza Glabra* (licorice) root extract, is used in the amount of 1% as a botanical skin lightener. Because the most commonly used pigment reducer, hydroquinone, is now considered unsafe for long-term use (and the FDA plans on banning it from nonprescription creams), there is a need for safe, herbal, pigment reducers. Glabridin also inhibits the formation of melanin, the brown pigment in the skin and is effective in managing hyperpigmentation. Glabridin also has an anti-inflammatory effect, as well as antioxidant, antifungal and antibacterial properties.

Silymarin, also referred to as silybin or silibinin, is a strong antioxidant and tyrosinase inhibitor present in extract of milk thistle. There is significant absorption of silymarin into the skin. Silymarin stimulates wound healing and there is evidence that silibinin, a flavonolignan from *silybum marianum*, can stimulate the removal of UVA damaged cells and prevent skin cancer. It also reduces UVB-induced DNA damage. Because of these effects, it may be useful as a supplement for sunscreen protection and for the treatment of radiation-induced inflammation and immunosuppression.

White Thyme Oil is a natural oil that possesses strong antibacterial properties, killing *Staphylococcus, Enterococcus, Escherichia*, and *Pseudomonas*. Beyond its use as an antibacterial, thyme is a potent antioxidant, antifungal and natural preservative. It is also a mosquito repellent.

Hyaluronic acid is a normal constituent of skin. It is a complex polysaccharide that has exceptional humectant properties, making it an effective moisturizing agent. As a moisturizer, it improves skin hydration and elasticity.[1] In addition, hyaluronic acid improves rosacea.[1] In a 0.2% concentration, it is effective in reducing skin inflammation, redness, and itching in seborrheic dermatitis.[1]

Glycerin is a common humectant in moisturizers. The diverse actions of the polyol glycerol on the epidermis include improvement of stratum corneum hydration, skin barrier function and skin mechanical properties, inhibition of the stratum corneum lipid phase transition, protection against irritating stimuli, enhancement of desmosomal degradation, and acceleration of wound-healing processes. Additionally, an antimicrobial effect has been demonstrated. Topical application of glycerol-containing products improves skin properties in diseases characterized by xerosis and impaired epidermal barrier function, such as atopic dermatitis. The increase of epidermal hydration by glycerol is critical in skin conditions aggravated by dry and cold environmental conditions, e.g. winter xerosis.

Example 1

The following listing of ingredients are provided as an exemplary, but non-limiting, embodiment of the present invention which is then produced under special conditions to reduce oxygenation and subsequent oxidation of l-ascorbic acid, as described hereinbelow.

| Phase | Ingredient | Quantity (% wt.) |
| --- | --- | --- |
| A010 | Deionized Water | 50-70 |
| B020 | Actiphyte of Licorice Root GL100NP (Product Code #322020-131) | .01-.3 |
| B030 | Disodium EDTA | 0.2 |
| B040 | Tetrasodium EDTA | 0.5 |
| B050 | Magnesium Sulfate Anhydrous | 0.2 |
| B060 | Sodium Bicarbonate | 0.2 |
| C070 | Xanthan gum | 0.3 |
| C080 | Hyaluronic Acid 93% | 0.05-2 |
| D090 | Pentylene Glycol | 5 |
| D100 | Glycerin 99.7% USP Kosher | .5-3 |
| D110 | silybin or silibinin | .1-2 |
| E120 | L-Ascorbic Acid USP/FCC | 10 |
| E130 | l(+)-Lactic acid | 8 |
| E140 | Citric Acid Anhydrous Granular USP FCC | 2 |
| E150 | Tartaric Acid, Granular, NF | 0.1-1 |
| F160 | Phenoxyethanol | 0.9 |
| F170 | White Thyme Oil, Organic | 0.001-.1 |
| G180 | Finsolv FTN | 1.25 |
| G190 | Liponate EHP | 1.25 |
| G200 | Vitamin A-Propionate 2.5 Mio IU/G (Retinyl-proprionate) | 0.2 |
| H210 | Sodium Hydroxide (30% Aqueous Solution) | 7.2 |
| | Glycyrrhiza Glabra (licorice) root extract | 0.05-.2 |

Regarding the G Phase Modifiers:
"Finsolv FTN" and "Liponate EHP" are emollient esters that impart a pleasant feel on the skin and aid in making the product cosmetically/aesthetically elegant.
In choosing emollient esters for practicing the present invention, one of ordinary skill in the art should be guided using those which do not require incorporation via an aggressive surfactant, to avoid all of the negatives typically associated with traditional emulsifiers, such as potential irritation, skin barrier damage, presence of 1,4 dioxane from ethoxylated materials, etc.

A serum of aqueous L-ascorbic acid further comprising retinyl propionate, glabridin, silibinin, thyme and hyaluronic acid which is pH stabilized to a range of from no less than 3.5 to about 3.7 using lactic acid, citric acid and tartaric acid, is prepared as follows:

Boil water for at least 15 minutes to remove oxygen from the water. Cool to ~35 degrees ° C. before beginning the batching.

Charge the water into a main reaction vessel and begin sparging the water with nitrogen. Maintain a nitrogen blanket over the solution throughout the remainder of the batch preparation.

Phase B, comprising glabridin, disodium EDTA, tetrasodium EDTA, magnesium sulfate and sodium bicarbonate, is introduced into the main reaction vessel and mix until completely dissolved and uniform. Mix for 5 minutes until uniform.

Charge Phase C to the batch. Begin to homogenize at LOW SPEED and add xanthan gum and hyaluronic acid, mixing until completely wet out, dispersed and uniform. Mix for 15 minutes or until uniform.

In a separate vessel, premix Phase D. When uniformly mixed, charge the premixture of the hydrolite, glycerin and Siliphos into the main vessel and homogenize until completely dispersed and uniform. Mix for 15 minutes or until completely uniform.

Charge Phase E to the batch. Add each ingredient, one at a time and mix for 5 minutes between additions. After the L(+)-ascorbic acid, L(+)-lactic acid, citric acid and tartaric acid have all been added, mix for an additional 10 minutes until completely uniform.

Charge Phase F to the batch. Add each ingredient, one at a time and mix for 5 minutes between additions. After the phenoxyethanol, and white thyme oil have all been added, mix for an additional 10 minutes until completely uniform.

In a separate vessel, premix Phase G. When uniformly mixed, Charge the premixture of the Finsolv FTN, Liponate EHP and retinyl propionate into the main vessel and homogenize until completely dispersed and uniform. Mix for 15 minutes or until completely uniform.

Using the 30% NaOH aqueous solution of Phase H begin to titrate the batch pH to 3.40 and 3.60 (Target 3.50). Pull approximately 1 Kg of the batch out and record the weight. If necessary, slowly adjust the pH of this sample to within the specified range using the NaOH 30% solution from Phase H. Using the weight of the sample pulled and the amount of NaOH 30% solution added in order to adjust the pH within specification, back-calculate the required amount of NaOH 30% solution for the main batch. If no pH adjustment is required, then return the product into the main batch and continue to mix slowly for an additional 5 minutes before proceeding.

Return the adjusted material into the main batch.

Begin to titrate any additional NaOH 30% solution (if required) into the batch to pH 3.40 and 3.60 (Target 3.50). Start with 50% of the calculated batch amount of NaOH. Allow to mix for 5 minutes and pull top and bottom samples of the batch to check the pH. If the pH of the top and bottom samples is not within acceptable limits mix for 5 minutes more and resample. Incrementally (no more than approximately ¼ of the required amount) add additional amounts of the NaOH solution to the batch until the pH 3.40 and 3.60 (Target 3.50) is achieved. Note the total quantity of the NaOH solution added to the batch. If less than the batch amount has been added QS the difference with deionized water that has been boiled to remove any dissolved oxygen.

Mix for 5 minutes after each addition of NaOH solution. Pull top and bottom samples of the batch for pH check. If the pH is not within accepted error range, continue mixing until the batch is uniform.

Pump the batch into appropriate cleaned and sanitized storage containers that have been sparged with nitrogen and closed with a nitrogen blanket on top/encompassing any headspace. Store in a cool dry location away from heat sources.

The stability of vitamin C has been the limiting factor in creating skin care products with biologically active vitamin C. The current invention has succeeded in increasing the shelf life of Vitamin C from the expected short shelf life of several days to at least 25 weeks, and even more than 50 weeks, in part by incorporating the following methodologies:

The preparation is housed in a light proof container.

The preparation has oxygen removed from water by boiling it off.

The preparation has nitrogen added back in to replace the gas dissolved in the water.

The preparation is prepared and stored under a cap of nitrogen.

The preparation is housed in a container that does not admit oxygen.

The preparation is stabilized both in light and dark with citric acid1

The preparation is refrigerated following production.

With this stabilization, the invention has succeeded in preserving the vitamin C at 82% levels of its original content after 5 months.

An important aspect of this invention is the creation of an effective combination of vitamin C, vitamin A, lactic acid, citric acid, silymarin, and glabridin in an acidic serum that performs a number of functions in the skin.

The specific use of high levels of alpha hydroxy acids allows for exfoliation aiding greater skin penetration of the other active agents, namely L ascorbic acid, Retinyl propionate, glabridin, and Silybin.

The L ascorbic acid, Retinyl propionate, alpha hydroxy acids, and Silybin are all small molecules with the ability to penetrate the skin and effect remarkable changes in the skin. Specifically, the agents smooth the skin, thin the stratum corneum, stimulate collagen synthesis thereby thickening the skin, inhibit tyrosinase thereby decreasing melanin production and lightening skin, and decrease wrinkles The current preparation is unique in that the combination of chemical methods (citric and tartaric acid being used as stabilizers); removal of oxygen by boiling the water and replacing it with nitrogen; capping the mixture with a blanket of nitrogen; using an air free and light opaque packaging; and refrigerating the mixture following its creation allow for unparalleled shelf life of the serum. Laboratory testing shows stability projected up to 2 years.

In Use:

One immediately observes smoothing of skin overnight by AHA exfoliants.

Exfoliants improve effectiveness of other AI by thinning stratum corneum. They also reduce brown and splotchy pigmentation.

Tyrosinase inhibition (decrease melanin): Vit. C, A, Glabridin and milk thistle. Usually takes many months to see clinical effect when used separately, but lightening is evident clinically in 2 months as opposed to 3-4 months when AHAs and Tyrosinase inhibition not done together.

Combined effect of collagen stimulation using AHAs and retinoid skin rejuvenation results in visible diminution in wrinkles beginning in about 6 months.

Providing a serum, rather than a cream, reduces likelihood of allergenicity as well as residue due to the reduced number of ingredients that could potentially cause reaction.

While most companies separate ingredients into many separate products, this invention allows for a simple, effective, skin care regimen. The superior results of the combination of this invention come from heretofore unseen synergism between components. The alpha-hydroxy acids allow for better penetration of the vitamin C, vitamin A, licorice and silymarin. This results in a more effective, quicker clinical effect. In addition, the citric and tartaric acids stabilize the vitamin C. The unique combination of these chemicals, as well as the anaerobic environment created by boiling off oxygen and capping the mixture with Nitrogen, along with the physical characteristics of packaging the mixture in a light and oxygen free environment and refrigerating the mixture following creation, allows for a prolonged period of stability of the notoriously unstable vitamin C. This allows for the use of the physiologically active form of vitamin C, namely L-ascorbic acid, as opposed to the vast majority of commercially available products which use chemically different and inactive forms of vitamin C.

The large percentage of active ingredients (over 20%) in this mixture is unique and the physical characteristics of a serum, as opposed to a gel or cream, allow for less irritation of the skin due to unwanted residue. The serum is light and dries within 20 seconds, thereby minimizing the chance of residual liquid vitamin C in solution staining clothing or bedsheets.

The unique combination of Vitamins C and A, 2 alpha-hydroxy acids, 4 tyrosinase inhibitors (L-ascorbic acid, Retinyl proprionate, silymarin, and licorice extract), and 5 antioxidants (vitamins C and A, silymarin, thyme, and licorice extract) provides for a rapid clinical effect. A decrease in skin roughness is apparent overnight, due to the exfoliative effects of the two alpha-hydroxy acids. Decrease in brown splotchy pigmentation, due to a decrease in melanin production, as well as exfoliation of previously created melanin, is visible as early as 2 months. Wrinkle reduction is visible as early as 6 months, due to the stimulation of collagen and elastin production by vitamin C, as well as anti-wrinkle effects of lactic and citric acids, and retinyl proprionate. The skin is maintained in a healthy condition with the addition of the moisturizing agents, glycerin and hyaluronic acid, and is less susceptible to environmental damage because of the 5 antioxidants.

One of skill in the art may substitute extracts from the Indian herb emblica for glabridin.

White thyme oil may be supplemented or possibly even replaced by oil of lavender, lemon oil, eucalyptol, clove oil, peppermint oil, bourbon oil, geranium oil and orange oil.

Silymarin may be supplemented with or replaced entirely by seabuckthorn oil, sage extract or grapeseed oil.

What is claimed is:

1. An aqueous topical serum having a pH of from 3.4 to 3.8 and comprising from 10% to 18% by weight of L(+)-ascorbic acid dissolved in substantially deoxygenated water, 0.2% by weight retinyl propionate, and from 0.005% to 0.5% by weight of a mixture of ingredients selected from the group consisting of glabridin, silibinin and thyme.

2. The serum of claim 1 wherein the pH is 3.4 to 3.7.

3. The serum of claim 1 wherein the pH is about 3.5.

4. The serum of claim 1 having a minimum percentage of at least 8% by weight active of L(+)-ascorbic acid remaining after at least 6 months.

5. The serum of claim 1 having a minimum percentage of at least 8% by weight active of L(+)-ascorbic acid remaining after at least 9 months.

6. The serum of claim 1 having a minimum percentage of at least 8% by weight active of L(+)-ascorbic acid remaining after at least 12 months.

7. The serum of claim 1 having at least 82% of active of L(+)-ascorbic acid compared to its original content after 5 months.

8. The serum of claim 1 wherein the oxygen in the substantially deoxygenated water has been replaced with nitrogen.

9. The serum of claim 1 wherein the L(+)-ascorbic acid is stabilized by the citric acid and the tartaric acid such that the level of active L(+)-ascorbic acid would be less in the same serum lacking the citric acid and/or the tartaric acid.

10. The serum of claim 1 that is capable of drying on the skin within 20 seconds of application.

11. The serum of claim 1 that is capable of intradermal delivery of 20 to 40 times as much L(+)-ascorbic acid as would be delivered to the dermal layer by systemic delivery of the same amount of L(+)-ascorbic acid.

12. The serum of claim 1 comprising 10% by weight of L(+)-ascorbic acid.

13. An aqueous topical serum having a pH in a range of from 3.4 to about 3.7 comprising from about 55% to about 61% by weight of substantially deoxygenated water, from 8% to about 18% of L(+)-ascorbic acid dissolved in the substantially deoxygenated water, 0.2% by weight retinyl propionate, 0.1% by weight of glabridin, 0.25% by weight of silibinin, 0.005% by weight of thyme, 8% by weight lactic acid, 2% citric acid, 0.4% tartaric acid, and from 5% to about 10% by weight NaOH.

14. The serum of claim 13 wherein the pH is about 3.5.

15. The serum of claim 13 having a minimum percentage of at least 8% by weight active of L(+)-ascorbic acid remaining after at least 6 months.

16. The serum of claim 13 having a minimum percentage of at least 8% by weight active of L(+)-ascorbic acid remaining after at least 9 months.

17. The serum of claim 13 having a minimum percentage of at least 8% by weight active of L(+)-ascorbic acid remaining after at least 12 months.

18. The serum of claim 13 having at least 82% of active of L(+)-ascorbic acid compared to its original content after 5 months.

19. The serum of claim 13 wherein the oxygen in the substantially deoxygenated water has been replaced with nitrogen.

20. The serum of claim 13 wherein the L(+)-ascorbic acid is stabilized by the citric acid and the tartaric acid such that the level of active L(+)-ascorbic acid would be less in the same serum lacking the citric acid and/or the tartaric acid.

21. The serum of claim 13 that is capable of drying on the skin within 20 seconds of application.

22. The serum of claim 13 that is capable of intradermal delivery of 20 to 40 times as much L(+)-ascorbic acid as would be delivered to the dermal layer by systemic delivery of the same amount of L(+)-ascorbic acid.

23. The serum of claim 13 comprising 10% by weight of L(+)-ascorbic acid.

\* \* \* \* \*